US008267867B2

(12) United States Patent
Abe et al.

(10) Patent No.: US 8,267,867 B2
(45) Date of Patent: Sep. 18, 2012

(54) ULTRASOUND IMAGE DIAGNOSIS APPARATUS AND DRIVE VOLTAGE SETTING METHOD FOR ULTRASOUND PROBE THEREOF

(75) Inventors: Yoshihito Abe, Tochigi-ken (JP); Tomohisa Imamura, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 5 days.

(21) Appl. No.: 13/044,667

(22) Filed: Mar. 10, 2011

(65) Prior Publication Data
US 2011/0224547 A1    Sep. 15, 2011

(30) Foreign Application Priority Data

Mar. 12, 2010   (JP) ................ P2010-056750

(51) Int. Cl.
*A61B 8/14* (2006.01)

(52) U.S. Cl. ...................... 600/459; 600/437

(58) Field of Classification Search ........... 600/437–469
See application file for complete search history.

(56) References Cited

U.S. PATENT DOCUMENTS

| 5,295,487 | A | * | 3/1994 | Saitoh et al. | 600/459 |
|---|---|---|---|---|---|
| 5,477,858 | A | * | 12/1995 | Norris et al. | 600/441 |
| 5,485,844 | A | * | 1/1996 | Uchibori | 600/455 |
| 5,860,927 | A | * | 1/1999 | Sakaguchi et al. | 600/453 |
| 6,171,246 | B1 | * | 1/2001 | Averkiou et al. | 600/458 |
| 6,210,335 | B1 | * | 4/2001 | Miller | 600/454 |
| 6,221,018 | B1 | * | 4/2001 | Ramamurthy et al. | 600/443 |
| 6,312,379 | B1 | * | 11/2001 | Bradley et al. | 600/437 |
| 6,612,989 | B1 | * | 9/2003 | Brock-Fisher | 600/447 |
| 6,824,518 | B2 | * | 11/2004 | Von Behren et al. | 600/443 |
| 7,850,609 | B2 | * | 12/2010 | Takimoto et al. | 600/437 |
| 2007/0112266 | A1 | * | 5/2007 | Kishimoto | 600/437 |

FOREIGN PATENT DOCUMENTS

JP   2003-070784   3/2003

* cited by examiner

*Primary Examiner* — Sanjay Cattungal
(74) *Attorney, Agent, or Firm* — Oblon, Spivak, McClelland, Maier & Neustadt, L.L.P.

(57) ABSTRACT

An ultrasound image diagnosis apparatus and a method for setting an ultrasound drive voltage by which appropriate probe motion parameters are established by individually estimating temperature changes which occur due to a plurality of heat sources existing within the probe. By individually storing or correcting relative temperature change data associated with motion parameters due to a plurality of heat source elements, an optimum driving voltage for the ultrasound transducers is set. Since a transmission drive voltage is larger than the conventional drive voltage can be set under a permissible probe temperature, image diagnosis can be improved.

10 Claims, 16 Drawing Sheets

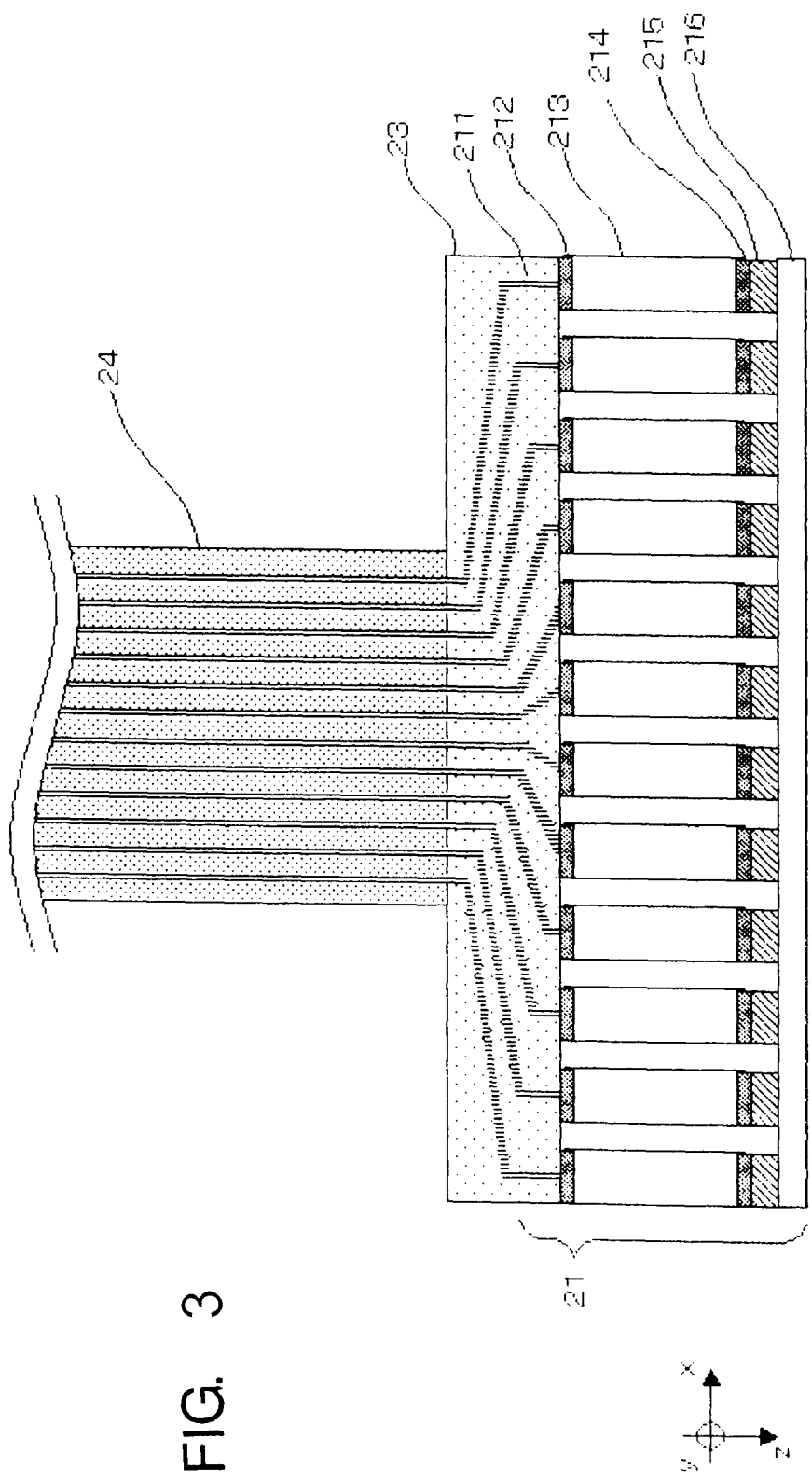

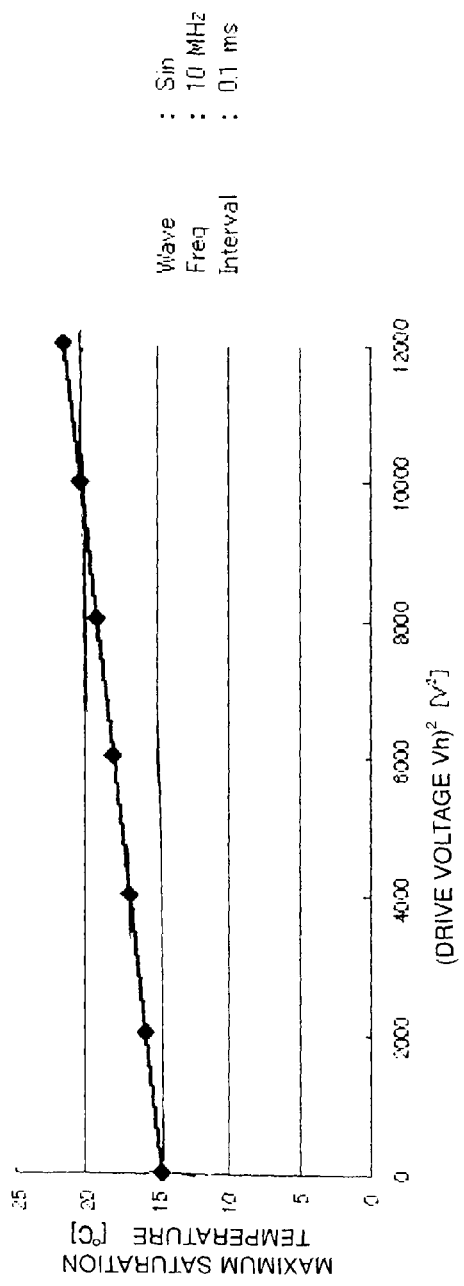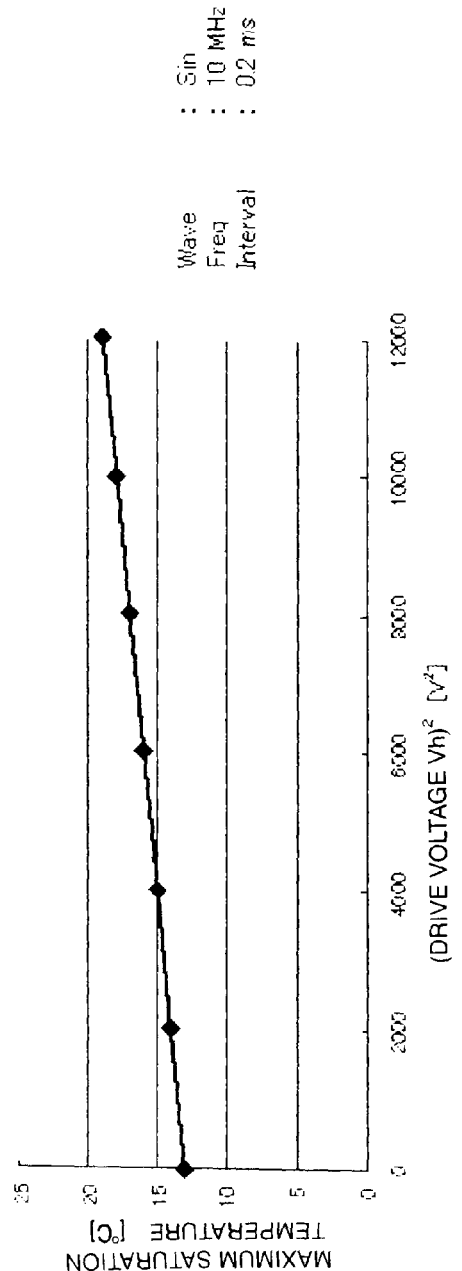

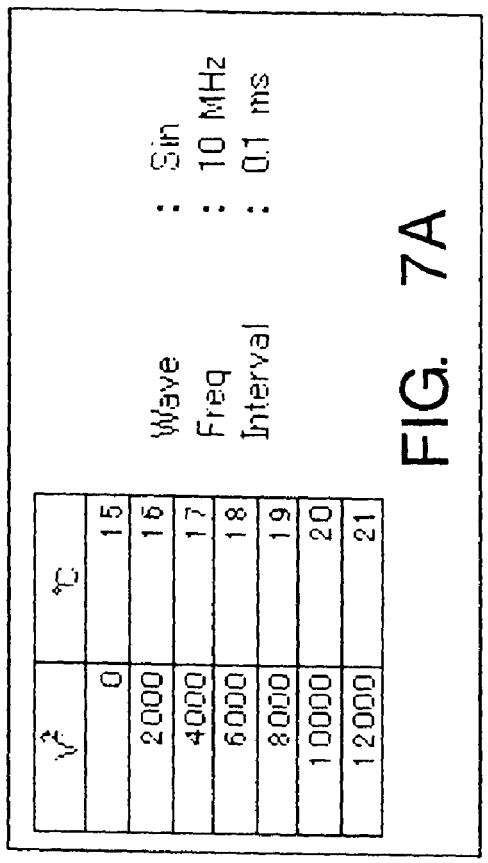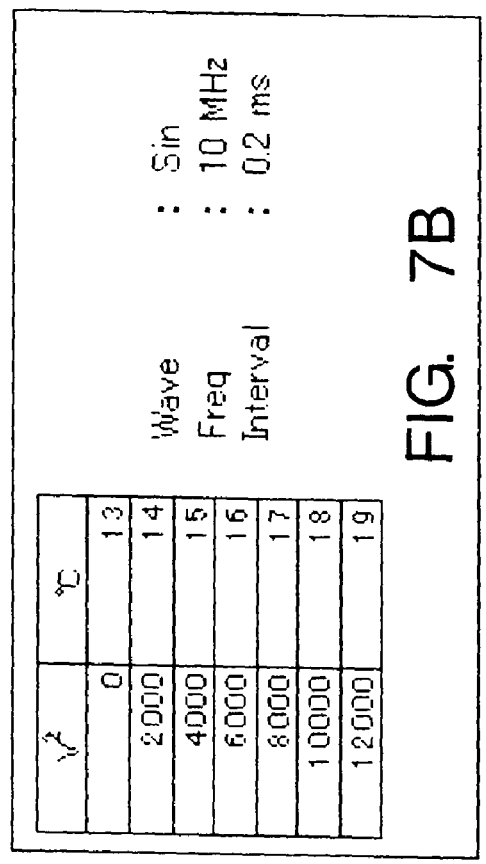
FIG. 7A
FIG. 7B

| SWING SPEED | 10deg | 15deg | 30deg |
|---|---|---|---|
| 0 | 15 °C | 14.5 °C | 14 °C |
| 5 | 14.75 °C | 14.25 °C | 13.75 °C |
| 10 | 14.25 °C | 13.75 °C | 13.25 °C |
| 15 | 13.75 °C | 13.25 °C | 12.75 °C |
| 20 | 13 °C | 12.5 °C | 12 °C |

FIG. 10

| SWspeed | °C |
|---|---|
| 0.1 | 13 |
| 0.2 | 14 |
| 0.3 | 15 |
| 0.4 | 16 |
| 0.5 | 17 |

FIG. 13

| SWING SPEED | 10deg | 15deg | 30deg |
|---|---|---|---|
| 0 | +10 ℃ | +10.5 ℃ | +11 ℃ |
| 5 | +10.3 ℃ | +10.8 ℃ | +11.3 ℃ |
| 10 | +10.8 ℃ | +11.3 ℃ | +11.8 ℃ |
| 15 | +11.3 ℃ | +11.8 ℃ | +12.3 ℃ |
| 20 | +12 ℃ | +12.5 ℃ | +13 ℃ |

FIG. 15

ULTRASOUND IMAGE DIAGNOSIS APPARATUS AND DRIVE VOLTAGE SETTING METHOD FOR ULTRASOUND PROBE THEREOF

CROSS-REFERENCE TO RELATED APPLICATIONS

This application claims the benefit of priority under 35 U.S.C §119(a) from Japanese Patent Application No. 2010-56750, filed on Mar. 12, 2010, the contents of which are expressly incorporated herein by reference in their entirety.

BACKGROUND OF THE INVENTION

A. Field of the Invention

The present invention relates to an ultrasound image diagnosis apparatus for performing diagnosis of the interior of an object by means of ultrasound waves and a drive voltage setting method for an ultrasound probe thereof.

B. Background of the Invention

An ultrasound image diagnosis apparatus typically transmits ultrasound via ultrasound transducers installed in an ultrasound probe (hereinafter, simply referred to as "probe") to an object, such as a patient, and receives reflected ultrasound waves (echo waves) which show differences in the acoustic impedances of the object's organs enabling the display of an image of the organs on a monitor. Ultrasound image diagnosis is performed by obtaining images on a display in real time from the simple touching of a probe to a patient body surface.

The ultrasound transmissions are performed by vibrating a plurality of ultrasound transducers installed in a probe. Due to the vibrations of the plurality of ultrasound transducers, a surface heat of the probe is inevitably increased. To ensure safety of an object who is touched by heat generated in the probe, international safety standards define an upper limit of a permissible surface temperature for an ultrasound probe. A conventional technique has proposed to provide a temperature sensor in the vicinity of the plurality of ultrasound transducers in order to limit ultrasound probe use within a scope of the permissible temperature. Thus, conventionally, the ultrasound transmission conditions have been decided in accordance with a result of temperature detection (for instance, see Japanese Patent Application Publication 2007-202077)

In the conventional ultrasound diagnosis apparatus, ultrasound images of two dimensions (2D) are generated by transmitting and receiving ultrasounds emitted from a plurality of ultrasound transducers arranged in one dimension (1D). Recently, three dimensional (3D) ultrasound images can be generated by performing ultrasound transmissions and receptions along two dimensions. By successively performing the ultrasound transmissions and receptions in two dimensions for generating ultrasound images, 3D ultrasound images can be displayed in real time.

To generate 3D ultrasound images, a mechanical 4D probe and a 2D array probe have been used. The mechanical 4D probe includes a plurality of ultrasound transducers arranged in a single (1D) direction, and the plurality of ultrasound transducers is swung in a direction orthogonal to the arranged direction of the plurality of transducers. To swing the ultrasound transducers, a driving unit, such as a stepping motor, is installed in the probe. In the 2D array probe, an array drive substrate is installed for supplying electric signals to each of the plurality of ultrasound transducers arranged in 2 directions.

Generally, since ultrasound probes used for an ultrasound diagnosis apparatus include a heat source, transmission conditions are decided in consideration of heat a generation limit under the international safety standard. Usually, ultrasound probes used for generating 3D ultrasound images include a plurality of heat sources including the plurality of ultrasound transducers. Thus, ultrasound transmission controls are performed by drive voltages controlled under relative temperatures to a surface temperature of the ultrasound probe. Consequently, since the ultrasound transmissions through the plurality of transducer are controlled by drive voltages that are closely controlled under the relative temperatures, it has been difficult to drive the transducers for operation at maximum possible sensitivity of the ultrasound probe for acquiring a target performance of the ultrasound diagnosis apparatus.

SUMMARY OF THE INVENTION

To solve the above-noted problems and drawbacks, an ultrasound diagnosis consistent with the present embodiment stores a plurality of temperature tables that individually estimate temperature changes generated by each of the plurality of heat sources. Thus, by estimating temperature changes, motion parameters for controlling the ultrasound transducers at an appropriate transmission voltage can be established. By controlling the transmission conditions within a scope of permissible temperature, a surface temperature of an ultrasound probe can be kept in a safe range. By setting the most appropriate motion parameters of an ultrasound probe, the ultrasound apparatus and the drive voltage setting method consistent with the present embodiments can increase sensitivity of the probe and can improve image qualities of the generated images.

Accordingly, there is provided one embodiment of an ultrasound image diagnosis apparatus including;

an ultrasound probe for transmitting and receiving a plurality of ultrasound waves along prescribed directions to and from an object:

an input unit configured to input at least one motion parameter for the ultrasound probe, wherein the at least one motion parameter includes at least one ultrasound waveform, a transmission interval, a transmission frequency or a focusing position of the plurality of ultrasound waves;

said ultrasound probe including a plurality of ultrasound transducers for respectively transmitting and receiving ultrasound waves in accordance with a designated motion parameter including and the drive voltage;

a drive component installed in the ultrasound probe for swinging the plurality of ultrasound transducers in order to change directions of the ultrasound transmissions and receptions in accordance with swing parameters, wherein the swing parameters includes at least one swing angle, a swing speed and an angular resolution;

a memory unit configured to store a first temperature change data for associating temperature changes due to the plurality of ultrasound transducers with the motion parameters, and a second temperature change data for associating temperature changes due to the drive component with the swing parameters for the drive component; and a control unit for setting the drive voltage based on the motion parameters, the swing parameters, the first temperature change data and the second temperature change data.

In another embodiment, there is provided an ultrasound image diagnosis apparatus including:

an ultrasound probe for transmitting and receiving a plurality of ultrasound waves along prescribed directions to and from an object:

an input unit configured to input at least one motion parameter including a driving voltage for the ultrasound probe;

a plurality of ultrasound transducers arranged in two dimensions and installed in the ultrasound probe for performing transmissions and receptions of ultrasound waves in accordance with the at least one motion parameter and the at least one transmission condition, wherein the at least one motion parameter includes of an at least one ultrasound transmission waveform, a transmission interval, a transmission frequency or a focusing position of the plurality of ultrasound waves;

a switching unit installed in the probe configured to switch electrical paths for transferring electrical signals to the plurality of ultrasound transducers based on at least one row parameter, wherein the at least one row parameter includes electrical signal transferring path data and a switching speed;

a memory unit configured to store a first temperature change data for associating temperature changes due to the plurality of ultrasound transducers with the at least one motion parameter, and a second temperature change data for associating temperature changes due to the switching unit with at least one row parameter; and a control unit configured to set a drive voltage based on the at least one motion parameter, the at least one row parameter, the first temperature change data and the second temperature change data.

Further, there is provided an embodiment of a probe drive voltage setting method for an ultrasound image diagnosis apparatus including an ultrasound probe having a plurality of transducers, a system control unit and a memory unit, the method comprising:

inputting either at least one swing parameter for the plurality of transducers or at least one row parameter for the plurality of transducers;

reading out a table of swing parameters vs. permissible temperatures or a table of row parameters vs. permissible temperatures from the memory unit based on the input;

calculating a limit value of the permissible temperatures from the table of swing parameters vs. permissible temperatures at the designated swing parameter, or a relative saturation temperature of the table of row parameters vs. permissible temperatures at the designated row;

reading out a table of transmission conditions vs. maximum saturation temperatures from the memory;

calculating a maximum drive voltage within the limit value of the permissible temperature or the relative saturation temperature by using a maximum saturation temperature at the input transmission condition; and driving the probe by using the maximum drive voltage and the input swing parameter or the row parameter.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIG. 3 illustrates a construction of a plurality of ultrasound transducers installed in the mechanical 4D probe.

FIG. 6A is a graph depicting a relationship between drive voltages and maximum saturation temperature in consistent with one embodiment.

FIG. 6B is a graph depicting a relationship between drive voltages and maximum saturation temperature in consistent with another embodiment.

FIG. 7A illustrates a table of temperature variations associated drive voltages with maximum saturation temperature shown in FIG. 6A.

FIG. 7B illustrates a table of temperature variations associated drive voltages with maximum saturation temperature shown in FIG. 6B.

FIG. 10 illustrates a table of temperature variation data associated swing parameters with upper limit of permissible temperatures.

FIG. 13 illustrates a table of temperature variation data associated row parameters with upper limits of permissible temperatures.

FIG. 15 is a table illustrating relationships between swing parameters and relative saturation temperatures.

DESCRIPTION OF PREFERRED EMBODIMENTS

Figure 1:
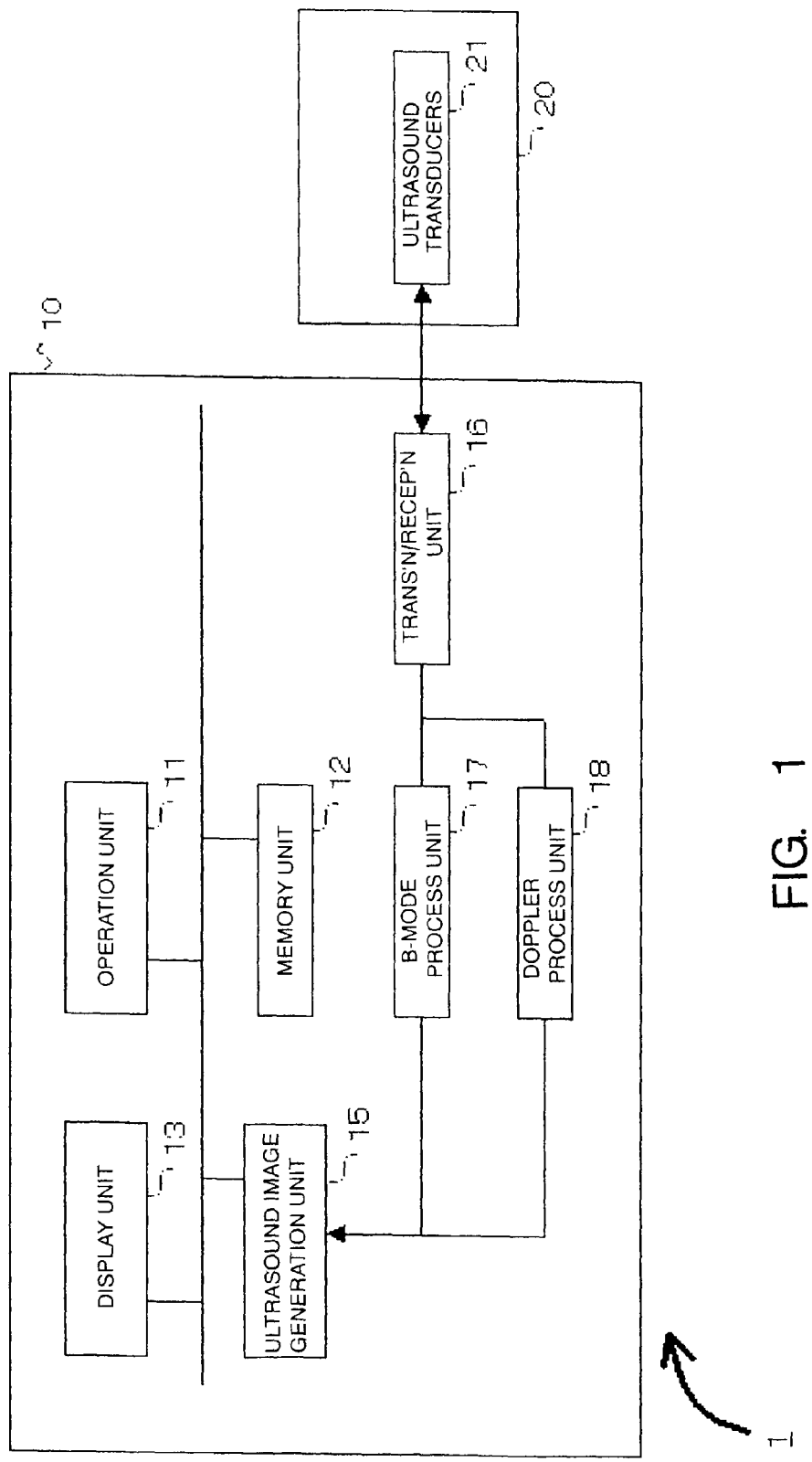
FIG. 1 is a block diagram illustrating an ultrasound diagnosis apparatus according to an embodiment of the present invention.

Referring now to the drawings, FIG. 1 is a block diagram illustrating a construction of an ultrasound diagnosis apparatus 1 consistent with one embodiment of the present invention. The ultrasound diagnosis apparatus 1 includes a system control unit 10 and a probe 20. The system control unit 10 includes an operation unit 11, a memory unit 12, a display unit 13, an ultrasound image generation unit 15, a transmission/reception unit 16, a B-mode process unit 17 and a Doppler process unit 18.

The probe 20 includes a plurality of ultrasound transducers 21. The probe 20 transmits ultrasound waves by means of the plurality of ultrasound transducers 21 based on transmission conditions and drive signals received from the transmission/reception unit 16. Further the probe 20 receives reflected ultrasound waves from an object and converts the reflected ultrasound waves to electric signals (hereinafter, "echo waves").

Figure 2A:
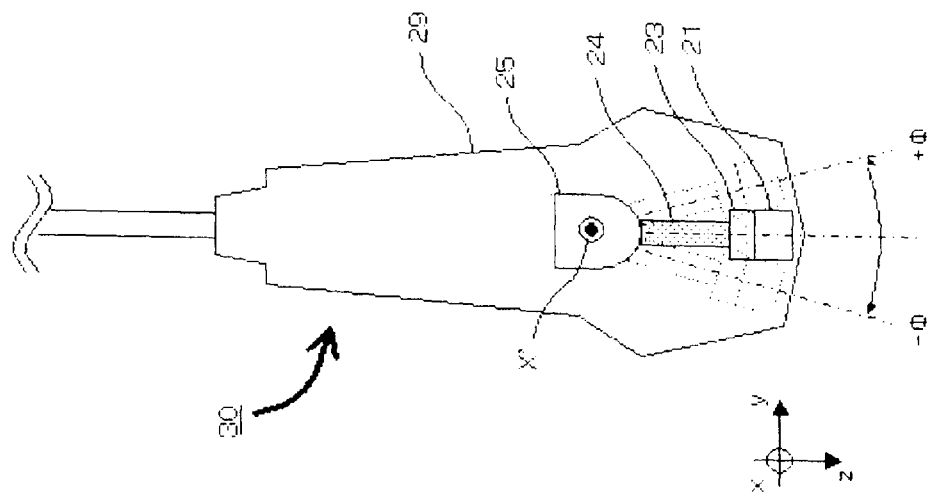
FIG. 2A is a cross-sectional view of a mechanical 4D probe along an x-z plane.
Figure 2B:
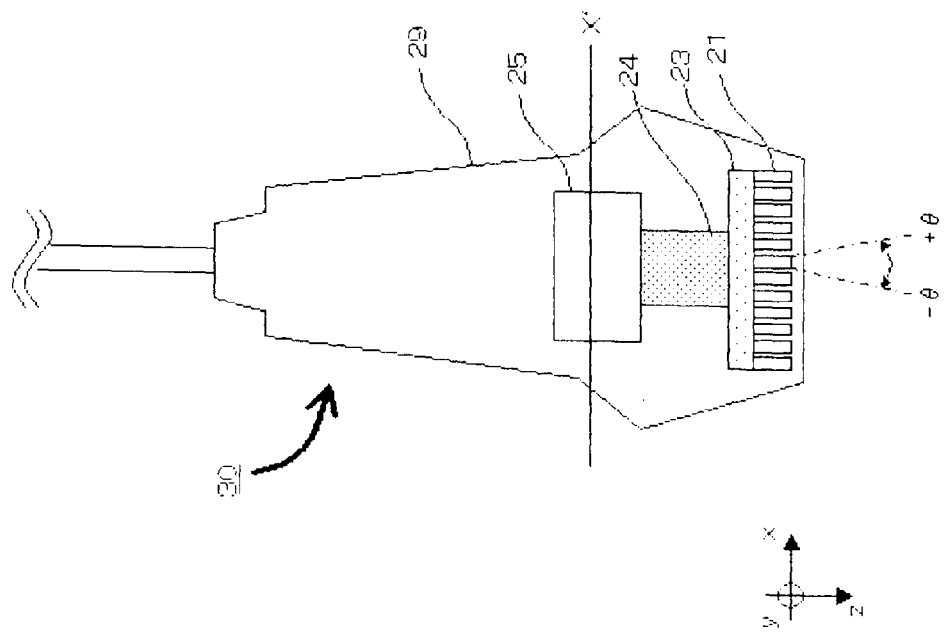
FIG. 2B is a cross-sectional view of the mechanical 4D probe along a y-z plane.
Figure 4A:
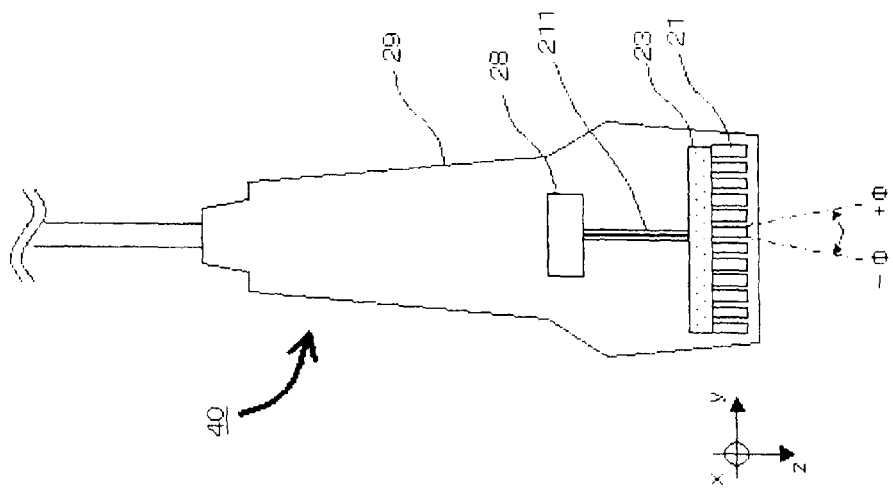
FIG. 4A is a cross-sectional view of a 2D array probe along an x-z plane.
Figure 4B:
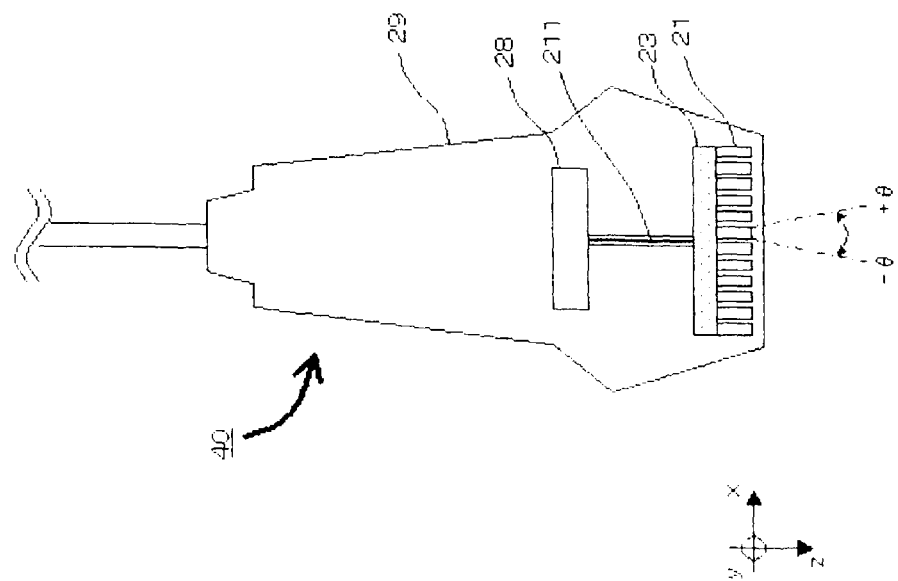
FIG. 4B is a cross-sectional view of a 2D array probe along a y-z plane.

To control directionalities of ultrasound transmissions and receptions along two dimensional directions, a mechanical 4D probe and a 2D array probe are used as the probe 20 for the ultrasound diagnosis apparatus consistent with the present embodiment. As illustrated in FIGS. 2A and 2B, the mechanical 4D probe is constructed by arranging a plurality of transducers in a single dimension (1D). Further, the mechanical 4D probe includes a drive unit 25 for swinging the plurality of ultrasound transducers 21 along an orthogonal direction to the single direction. As illustrated in FIGS. 4A and 4B, the 2D array probe 40 includes a plurality of ultrasound transducers 21 arranged in two dimensions (2D). To perform ultrasound transmission and reception, the 2D array probe 20 further includes a drive board for switching rows of the ultrasound transducers 21 so as to vary the ultrasound transmission and reception directions along 2 dimensions.

In the following embodiments, such driving voltages of ultrasound transducers, swing parameters for designating swinging conditions of the drive unit for the mechanical 4D probe and row parameters for designating which row of the transducers should be driven, are collectively referred to as motion parameters for the probe.

The transmission/reception unit 16 for supplying drive signals to the probe 20 includes pulsar circuits and delay circuits (both are not shown). Pulsar circuit repeatedly generates rate pulses for transmitting ultrasound waves to the probe 20. Delay circuits add delay times to the rate pulses for determining a transmitting directionality by converging ultrasounds in a beam shape. The transmission/reception unit 21 supplies the rate pulses with added delay times to the probe 20 as drive signals. The drive signals include transmitting conditions data for designating drive parameters of the ultrasound transducers 21. The transmitting conditions include, for example, an ultrasound transmission wave form, transmission intervals, a transmission frequency and a focusing position of ultrasounds.

When a mechanical 4D probe 30 is connected to the system control unit 10, the drive signals include swing parameter data for designating swing conditions for the drive unit 25. The swing parameters include, for example, swing angle data for the ultrasound transducers by the drive unit, swing speed data, and angular resolution data. The angular resolution is a parameter for designating ultrasound transmissions and receptions at particular degrees of tilting angle of the ultrasound transducers.

When a 2D array probe 40 is connected to the system control unit 10, the drive signals include row parameter data for designating which row of ultrasound transducers 21 in the 2D array should be driven. The row parameters include such data as switching speeds and switching orders of signal paths among the plurality of ultrasound transducers.

The transmission/reception unit 16 further includes an amplification circuit for amplifying echo waves received through the probe 20, an A/D converter and an adder (each not shown). The A/D converter delays the echo waves necessary for deciding directionality of the signals. The adder accumulates the delayed signals for generating echo waves corresponded to each scanning line of the ultrasound transmissions. The transmission/reception unit 16 generates and supplies echo waves to the B-mode process unit 17 or the Doppler process unit 18.

When a mechanical 4D probe 30 is connected to the system control unit 10, the echo waves output from the transmission/reception unit 16 are associated with the tilt angle of the ultrasound transducers 21 at a reception time of the ultrasound through the ultrasound transducers 21. The tilt angle data is used for generating 3D images in the ultrasound image generation unit 15. When a 2D array probe 40 is connected to the system control unit 10, echo waves output from the transmission/reception unit 16 are associated with row data of the ultrasound transducers 21 receiving the ultrasound waves. The row data is used for generating 3D images in the reflected ultrasound image generation unit 15.

B-mode process unit 17 generates B-mode signals that vary in response to amplitude intensity of echo waves output from the transmission/reception unit 16. The B-mode signals generated from the B-mode process unit 17 are output to the ultrasound image generation unit 15.

Doppler process unit 18 detects frequency transitions of echo waves and generates Doppler signals by subtracting moving speeds of tissues or blood flows. Doppler signals output from the Doppler process unit 18 are supplied to the ultrasound image generation unit 15.

The ultrasound image generation unit 15 generates ultrasound images based on B-mode signals or Doppler signals supplied from the B-mode process unit 17 or the Doppler process unit 18. Generation of the ultrasound images is performed by changing an image generation mode in accordance with a mode switching signal instructed through the operation unit 12. For instance, when the operation unit 12 designates a B-mode, the ultrasound image generation unit 15 generates B-mode images by mapping B-mode signals on the coordinate corresponding to the ultrasound transmissions and receptions. When the operation unit 12 designates a Doppler mode, the ultrasound image generation unit 15 generates Doppler images by mapping Doppler signals on the coordinate corresponding to ultrasound transmissions and receptions and further by overlapping on the B-mode images. The generated ultrasound images in the ultrasound image generation unit 15 are supplied to the display unit 14.

When a mechanical 4D probe 30 is connected to the system control unit 10, the ultrasound image generation unit 15 generates respective ultrasound images in accordance with each tilt angle of the ultrasound transducers 21 at receiving times of the respective echo waves. For instance, when the ultrasound transducers 21 receive echo waves at 128 different tilt angles, the ultrasound image generation unit 15 generates 128 ultrasound images, each for a respective tilt angle. Further, the ultrasound image generation unit 15 generates 3D volume data by composing each of ultrasound images by using the tilt angle data. Practically, volume data is generated by mapping each pixels of an ultrasound image on a voxel at a predetermined position by using the data tilt angle data.

When a 2D array probe 40 is connected to the system control unit 10, the ultrasound image generation unit 15 generates respective ultrasound images in accordance with each row of the ultrasound transducers 21 used for receiving echo waves. For instance, when each of the ultrasound transducers 21 arranged in 64 rows receives respective echo signal, the ultrasound image generation unit generates respective ultrasound images for each of the 64 rows. The ultrasound image generation unit 15 generates 3D volume data by composing each ultrasound images by using the row data. Thus, a volume data is generated by mapping each pixels of the ultrasound image with a voxel at a prescribed position by using row data. The ultrasound image generation unit 15 converts volume data to image data based on various rendering processes and outputs to the display unit 13 or the memory unit 12.

In this embodiment, ultrasound image generation unit 15 generates B-mode images and Doppler images in accordance with a mode switching signal. Of course, the ultrasound image generation unit 15 can generate other ultrasound images, such as color Doppler imaging (CDI) mode images or M mode images. Color Doppler imaging (CDI) mode generates colored images by calculating frequency transitions in echo waves based on parameters, such as moving speeds, dispersion or amplitudes of tissues or blood streams among the areas in the echo waves. M mode displays changes of echo wave strengths at a particular diagnosis region. It is also possible to display a B-mode image or a Doppler image with an ultrasound image of another mode in parallel after generating ultrasound images of the B-mode or a Doppler mode.

The display unit 13 is constructed by, for example, a liquid crystal display (LCD) or an electro luminescence (EL) display. The display unit 13 displays ultrasound images output from the ultrasound image generation unit 15. Further the display unit 13 displays the displaying parameters for ultrasound images of the ultrasound image generation unit 15 or the ultrasound transmission and reception parameters for the probe 20.

The memory unit 12 is constructed by, for instance, a ROM, a RAM, a flash memory as an erasable nonvolatile memory and a HDD (hard disk drive). The memory unit 12 stores various application data and control data executed by the system control unit 10 and volume data or image data supplied from the ultrasound image generation unit 15. Further, the memory unit 12 stores a table of transmission conditions vs. maximum saturation temperatures which associates transmission conditions with maximum saturation temperature. When a surface temperature of the probe 20 reaches to an equilibrium state after successively driving the ultrasound transducers 21 under certain transmission conditions, the transmission conditions vs. maximum saturation temperature table records the saturation temperature of the ultrasound transducers 21 corresponding to the transmitting conditions.

When a mechanical 4D probe 30 is connected to the system control unit 10, the memory unit 12 stores swing parameters associated with permissible temperatures in a table of swing parameters vs. permissible temperatures. The table of swing parameters vs. permissible temperatures records a permissible temperature of the ultrasound transducers 21 that is an allowable limit temperature for keeping safety of an object when a mechanical 4D probe 30 is driven at a certain swing parameter.

When a 2D array probe 40 is connected to the system control unit 10, a table of row parameters vs. permissible temperatures is stored in the memory unit 12 in order to associate row parameters with permissible temperatures. The table of row parameters vs. permissible temperatures records a permissible temperature of the ultrasound transducers 21 that is an allowable limit temperature for keeping safety of an object when the 2D array probe 40 is driven at a certain row parameter.

The memory unit 12 can store other tables, such as, a table of swing parameters vs. relative saturation temperatures in which the swing parameters are associated with the temperature changes of the drive unit 25 or a table of row parameters vs. relative saturation temperatures in which the row parameters are associated with the temperature changes of the drive board 28.

The operation unit 11 is constructed by using various operation devices, such as mechanical buttons, dials, a track ball or a slider. The operation unit 11 converts inputted electrical signals for supply to the system control unit 10. The operation unit 11 outputs instruction signals for instructing start and stop of ultrasound transmission and reception to the transmission/reception unit 16 or ultrasound image generation mode switching instruction signals to the ultrasound image generation unit 15, and instruction signals of transmitting conditions or instruction signals of swing parameters.

FIG. 2A is cross-sectional view of the mechanical 4D probe 30 along the x-z plane where the x-axis indicates an arranging direction of the ultrasound transducers 21 and the z-axis indicates a center of ultrasound emission direction form the ultrasound transducers 21. FIG. 2B is a cross-sectional view of the mechanical 4D probe 30 along the y-z plane.

The mechanical 4D probe 30 includes ultrasound transducers 21, a backing material 23, an arm 24 and a drive unit 25. The ultrasound transducers 21 are arranged in a single direction along the x-axis and connected to the backing material 23. Further, the backing material 23 is coupled to the drive unit 25 through the arm 24. The mechanical 4D probe 30 is constructed by including these elements in a probe envelope 29.

The ultrasound transducers 21 transmit ultrasound signals in the z-direction in accordance with signal inputs from the transmission/reception unit 16, and receive reflected ultrasound waves reflected from an object. By converting the reflected waves to electrical echo waves, the ultrasound transducers 21 output the electrical signals to the transmission/reception unit 16. The transmission/reception unit 16 varies directionalities of the ultrasound waves transmitted from the ultrasound transducers 21 (FIG. 1) by giving appropriate delays to the electrical signals. The ultrasound directionality varies between the tilt angles from $(+\theta)$ degrees to $(-\theta)$ degrees in the z-axis.

The ultrasound transducers 21 are connected to the backing material 23. The backing material supports the ultrasound transducers 21 and absorbs unnecessary ultrasounds emitted in the opposite z direction from the ultrasound transducers 21. The backing material is made of an ultrasound absorbing material, such as a ferrite rubber.

The backing material 23 is coupled to the drive unit 25 through the arm 24. The drive unit 25 may be a motor for performing rotation movements by receiving electrical signals. One edge of the motor is connected to the arm 24. The drive unit 25 rotates along a center axis X' in accordance with electrical signals output from the transmission/reception unit 16. As illustrated in FIG. 2B, the arm 24 is swung between the angles from $(+\Phi)$ degrees to $(-\Phi)$ degrees in the y-axis at a center of z-axis by the rotation movement of the drive unit 25. Thus, the ultrasound directionalities of the transmissions and receptions through the ultrasound transducers 21 vary between the angles from $(+\Phi)$ degrees to $(-\Phi)$ degrees with swinging of the drive unit 25.

The ultrasound transducers 21 vary directionalities along the x-axis direction by using delayed signals. And the ultrasound transducers 21 vary directionalities in the y-axis direction by the swing of the drive unit 25. Consequently, to perform ultrasound transmissions and receptions in 2 dimensions along the x-y plane, the ultrasound transducers 21 are moved by controlling the delayed amounts of the electrical signals and the swinging angles.

To swing the drive unit 25, the transmission/reception unit 16 supplies electrical signals to the drive unit 25. While the drive unit 25 converts the electrical signals to swinging energy power for the ultrasound transducers 21, some portion of the electrical energy generates heat emitted through the drive unit 25. The emitted heat is transferred to each components connected to the drive unit. Consequently, a surface temperature of the probe envelope 29 of the mechanical 4D array probe 30 rises.

As illustrated in FIG. 3, the ultrasound transducer 21 is constructed by combining an acoustic lens 216, a plurality of matching layers 215, a plurality of grounding electrodes 214, a plurality of transducers 213, a plurality of signal electrodes 212 and a plurality of leads 211. The acoustic lens 216 focuses the transmission ultrasound waves and reception ultrasound waves at a prescribed distance. The acoustic lens 216 is made of, for example, a silicon rubber that has acoustic impedance substantially equal to tissues of a living body. The plurality of matching layers 215 performs the acoustic impedance matching between the transducers 213 and the living body tissues. The matching layers 215 are provided between the plurality of transducers 213 and the plurality of acoustic lens 216 by attaching a plurality of components of different acoustic impedances. The grounding electrode 214 is connected to a grounding terminal (not shown) of the ultrasound diagnosis apparatus 1 through a grounding line of the leads 211. The transducers 213 are vibrated by the electrical signals supplied from the signal electrodes 212 and transmit ultrasounds depending on the supplied frequency. Each of the signal electrodes 212 is provided between the lead 211 and the transducers 213 for transmitting an electrical signal inputted from the lead 211 to the transducers 213. The lead 211 of a wire is provided on a surface of the backing material 211 to transmit electrical signals between the signal electrodes 212 and the transmission/reception unit 16.

To transmit and receive ultrasound waves, the transmission/reception unit 16 supplies electrical signals to the transducers 213. While the transducers 213 convert the electric energy of the electrical signals into acoustic vibrations, some portion of the electric energy is emitted from the transducers 213 as heat. The generated heat is transferred to each component connected to the transducers 213. Consequently, a temperature of the probe envelope 29 rises. The ultrasound waves transmitted from the transducers 213 are absorbed by the backing material 23. Reflected ultrasound waves reflected from an object are absorbed by the transducers 213 through the acoustic lens 216. Vibrations of the transducers upon the absorption of reflected ultrasound waves generate heat and raise the surface temperature of the mechanical 4D array probe 30.

Figure 5:
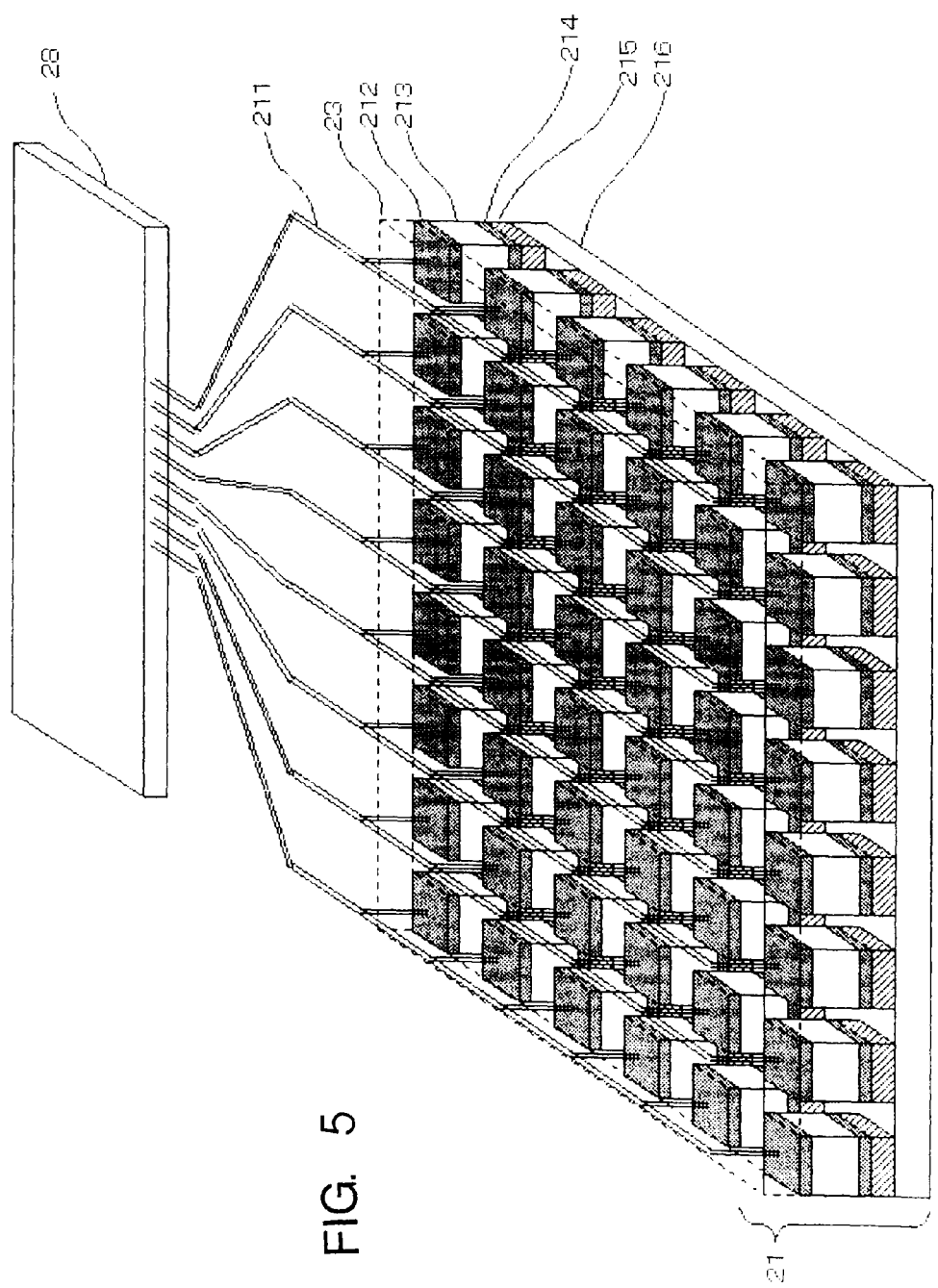
FIG. 5 illustrates a construction of ultrasound transducers installed in a 2D array probe.

With reference to FIGS. 4A, 4B and 5, construction of a 2D array probe 40 will be explained by supposing that a center ultrasound transducer 21 emits ultrasound waves along z-axis. FIG. 4A is a cross-sectional view of 2D array probe 40 along x-z plane. FIG. 4B is a cross-sectional view of 2D array probe 40 along a y-z plane. In 2D array probe 40, a plurality of ultrasound transducers 21 is arranged along the x-axis and the y-axis. The 2D arranged ultrasound transducers 21 are connected to a backing material 23. Further, the backing material 23 is coupled to a drive board 28 through a plurality of leads 211 in order to supply electrical signals to the respective ultrasound transducers 21. These components are covered by a probe envelope 29.

Ultrasound transducers 21 transmit ultrasounds in z-direction in accordance with electrical signals supplied from the transmission/reception unit 16. The transmission/reception unit 16 controls to vary directionalities of ultrasound waves transmitted from the ultrasound transducers 21 by appropriately delaying electrical signals supplied to the ultrasound transducers 21. The directionality of ultrasound waves tilts between angles from (+θ) degrees to (−θ) degrees in the x-axis direction from a center of the z-axis and also tilts angles between (+Φ) degrees to (−Φ) degrees in the y-axis direction. Further, ultrasound transducers 21 receive reflected ultrasound waves reflected from an object and convert to electrical echo waves for outputting to the transmission/reception unit 16.

The ultrasound transducers 21 are coupled to a drive board 28 through the backing material 23 and the lead 211. The drive board 28 switches which row of ultrasound transducers 21 in turn is supplied by the electrical signals in accordance with the drive signals output from the transmission/reception unit 16. Thus, by selecting ultrasound transducers 21 for transmitting and receiving ultrasounds by using the drive board 28, 2D ultrasound transmissions and receptions can be performed on the x-y plane.

FIG. 5 shows a construction of a plurality of transducers used in a 2D array probe. The ultrasound transducers 21 is constructed by combining an acoustic lens 216, a plurality of matching layers 215, a plurality of grounding electrodes 214, a plurality of transducers 213, a plurality of signal electrodes 212 and a plurality of leads 211. The ultrasound transducers 21 are arranged in two dimensions. Each of the leads 211 connected to a respective electric signal electrode 212 is connected to the drive board 28.

The transmission/reception unit 16 supplies electrical signals to the drive board 28 for performing switching operations. The drive board 28 performs the switching operations in accordance with row parameters included in the electrical signals. Due to the switching operations, many electrical signals are input and output to and from the drive board 28 at high speed. These inputs and outputs of the electrical signals generate heat. The generated heat is emitted from the drive board 28. Thus, the emitted heat transfers to each element connected to the drive board 28. Consequently, a surface temperature of the 2D array probe 40 rises.

When the ultrasound transmissions and receptions are performed by using the ultrasound transducer shown in FIG. 5, heat is generated due to energy conversion by the transducer to produce acoustic vibration. The heat emitted from the transducers 213 is transferred to each component connected to the transducers 213, and consequently, increases the temperature of the probe envelope 29. Further, the ultrasound waves transmitted from the transducers 213 are absorbed in the backing material 23. And the echo waves reflected from an object are absorbed in the transducers 213 through the acoustic lens 216. The vibration in accompanying these absorptions generates heat transferred through each of components to increase the temperature of the probe envelope 29. Thus, a surface temperature of the 2D array probe 40 rises.

As explained above, to transmit and receive ultrasound waves in 2 dimensions, a probe 20 includes a plurality heat sources other than the ultrasound transducers 2. For instance, a drive unit 25 becomes a heat source in a mechanical 4D probe 30, and drive board 28 becomes a heat source in a 2D array probe 40. To appropriately control temperature increases due to the plural heat sources including the ultrasound transducers 21, the memory unit 12 in the ultrasound diagnosis apparatus 1 stores a table of transmitting conditions vs. maximum saturation temperatures and a permissible temperature table. The table of transmitting conditions vs. maximum saturation temperatures records temperature changes that are generated when the ultrasound transducers 21 are driven at certain motion parameters. The permissible temperature table records temperature changes and changes of permissible temperatures that are generated when the heat sources, such as drive unit 25 or the drive board 28, are driven at certain motion parameters. Firstly, the system control unit 10 reads out the permissible temperature and calculates an upper limit of the permissible temperatures when the probe 20 is driven at a designated swing parameter or a row parameter. Then, the system control unit 10 reads out the transmitting conditions vs. maximum saturation temperatures and decides a drive voltage for the ultrasound transducers 21 so that the maximum saturation temperature falls within a range of permissible temperatures. When the drive voltage is decided, the system control unit 10 drives the probe 20 by using the designated swing parameters or the row parameters, the transmitting conditions and the decided drive voltage.

FIGS. 6A and 6B are graphs showing relationships between transmitting conditions and maximum saturation temperatures. FIG. 6A shows the relationships between the drive voltages and the maximum saturation temperatures when a sine curve is used as the transmission wave form at 10 MHz of transmission frequency and 0.1 ms of transmission intervals. FIG. 6B shows the relationships between the drive voltages and the maximum saturation temperatures when a sine curve is used as the transmission wave form at 10 MHz of transmission frequency and 0.2 ms of transmission intervals. In the present embodiments, the maximum saturation temperature is an equilibration status temperature that reaches when the ultrasound transducers 21 are successively driven at the same transmitting conditions. The heat generation by the ultrasound transducers 21 largely changes depending on the supplied drive voltages. As illustrated in FIG. 6, when the drive voltage becomes larger, the amount of heat generation becomes larger. Further, the maximum saturation temperatures vary depending on the transmitting conditions for driving the ultrasound transducers 21. As shown in FIGS. 6A and 6B, when the ultrasound transmission interval is changed from 0.1 ms to 0.2 ms, the maximum saturation temperatures is lowered.

The memory unit 12 stores such relationships between the drive voltages of the transmitting conditions and the maximum saturation temperatures as tables. FIGS. 7A and 7B show exemplary tables of the transmitting conditions vs. maximum saturation temperature for different transmission intervals. In memory unit 12, a plurality of tables corresponding to the same number of transmitting conditions are stored for indicating the relationship between the drive voltage and the maximum saturation temperature. Accordingly, when other transmitting conditions are applied to the probe, the memory unit 12 stores corresponding relationships between the drive voltages and the maximum saturation temperatures as the table of transmitting conditions vs. maximum saturation temperatures. For instance, the probe may be driven under the transmitting condition by using a square wave as a transmission wave form at 12 MHz of transmission frequency and 0.3 ms of transmission intervals.

By reading out the table of transmitting conditions vs. maximum saturation temperatures from the memory unit 12, the system control unit 10 can calculate the maximum saturation temperature for the ultrasound transducers 21 when the transmitting conditions and the drive voltage are decided.

Figure 8:
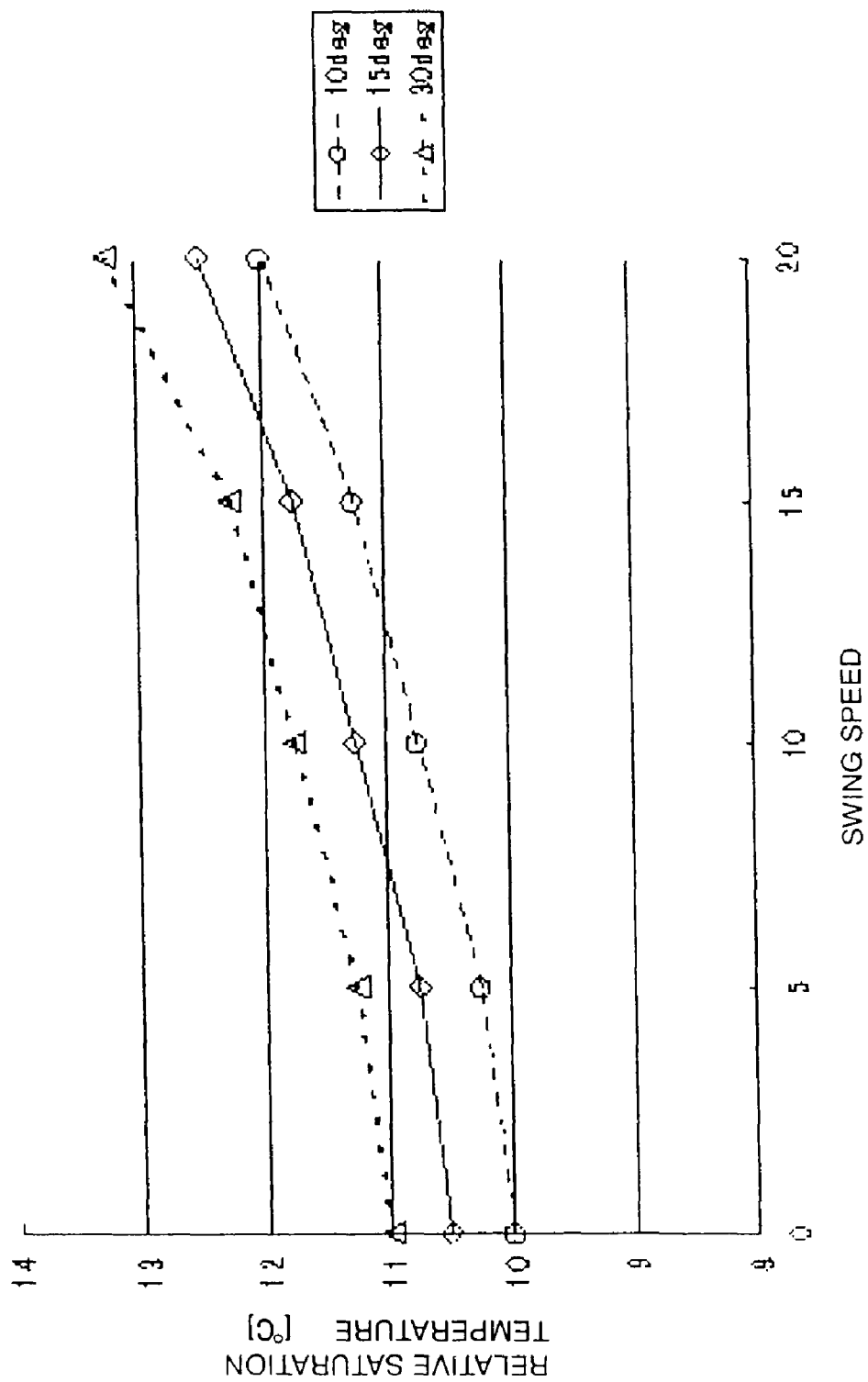
FIG. 8 is a graph depicting relationships between swing parameters and relative saturation temperatures.

FIG. 8 is a graph showing relationships between the swing parameters and the relative saturation temperatures. FIG. 8 shows relationships between the swing speeds and the relative saturation temperature when the swing angles are respectively set at 10 degrees, 20 degrees and 30 degrees. In the present embodiment, the relative saturation temperature is a temperature difference between the equilibration status temperature of the ultrasound transducers 21 reached by successively driving the drive unit 25 under the same swing parameter and the temperature of the ultrasound transducers 21 that are not driven by the drive unit 25. The larger the swing speed and the larger the swing angle are applied to the drive unit 25, the larger the amount of heat is generated in the ultrasound transducers. In accordance with the larger amount of heat generated by the drive unit 25, the relative saturation temperature increases and the ultrasound transducers 21 also increase in temperature.

Both heat generations of the ultrasound transducers 21 and the drive unit 25 increase a temperature of the probe envelope 29. Consequently, to assure the safety of an object, it is necessary to keep the temperature of the probe envelope 29 under a certain safe value by estimating the temperature changes due to the two heat sources. In the present embodiment, the ultrasound diagnosis apparatus controls the probe temperature by setting a parameter of permissible temperature. The permissible temperature indicates a scope of temperature of the ultrasound transducers 21 that can keep the object safe. The system control unit 10 maximizes the drive voltage for the ultrasound transducers within a scope of an upper limit value of the permissible temperature. By doing so, it becomes possible to increase the sensitivity and quality of the generated ultrasound images while the temperature of the probe envelope 29 is kept under the upper limit of permissible temperature for keeping the object safe.

If the probe 20 installs the ultrasound transducers 21 alone as the heat sources, the permissible temperature becomes a constant value. In this case, the system control unit 10 can set the maximum drive voltage by an upper limit of the permissible temperature at the designated transmitting conditions. When other heat sources, such as the drive unit 25 or the drive board 28 are installed in the probe 20, the permissible temperature of the ultrasound transducers 21 is reduced in accordance with the increase in heat generation due to the added heat sources. In the present embodiment, as explained above, the temperature changes of the heat sources are estimated by using the permissible temperature table for setting the permissible temperature.

Figure 9:
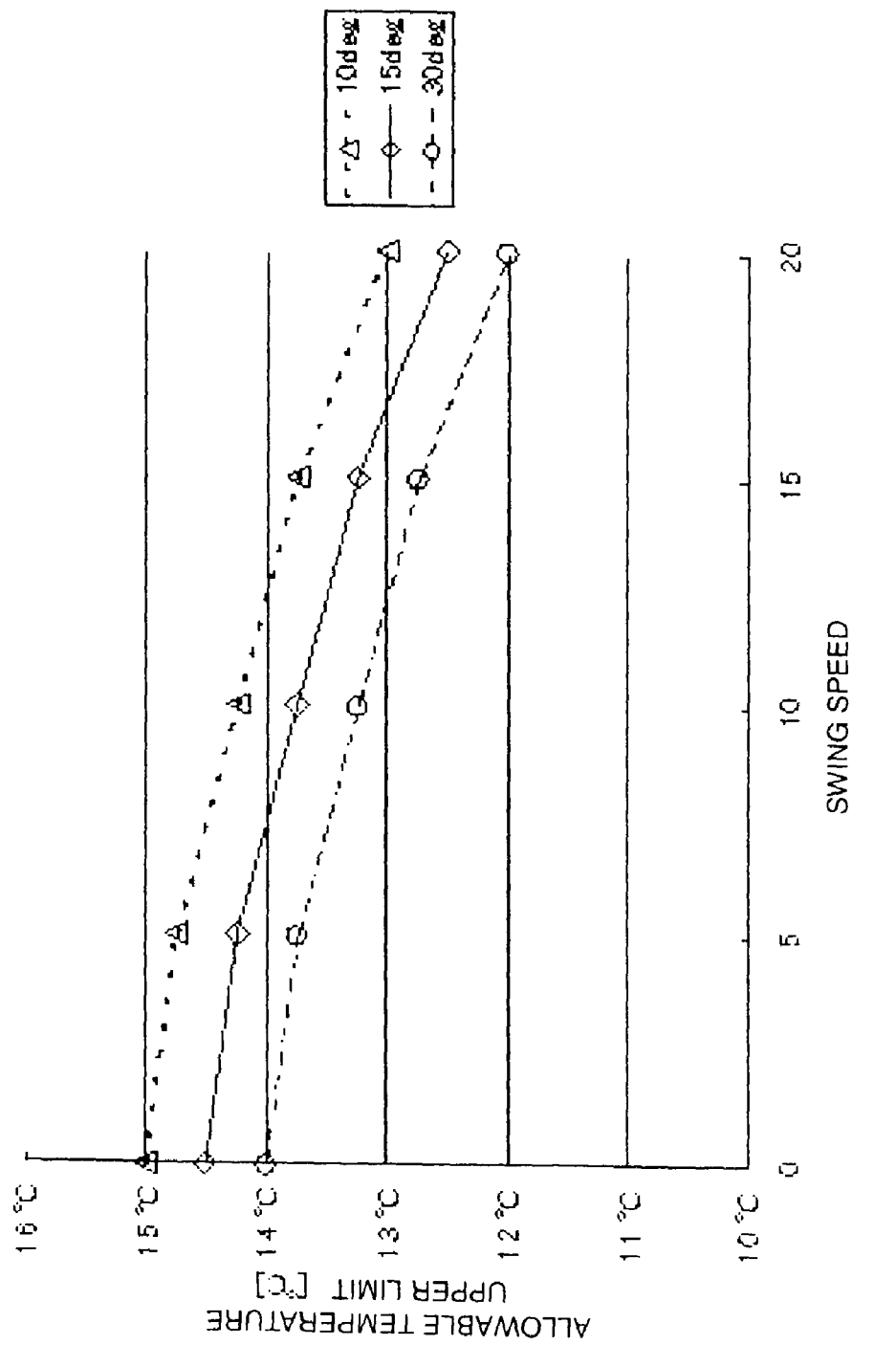
FIG. 9 is a graph depicting relationships between swing parameters and an upper limit of permissible temperatures.

FIG. 9 is a graph showing relationships between the swing parameter and the permissible temperatures. As shown in FIG. 8, the heat generation of the drive unit 25 becomes larger in proportion to the swing speed and the swing angle. Consequently, as shown in FIG. 9, the permissible temperature of the ultrasound transducers 21 for keeping an object safe becomes small in proportion to the swing speed and the swing angle. Thus, the change of the permissible temperatures can be obtained from the differences between the permissible temperature without the drive unit 25 and the relative saturation temperature of the drive unit 25. FIG. 10 is an exemplary table of swing parameters vs. permissible temperatures. In the table, permissible temperatures of the ultrasound transducers 21 are stored in accordance with the swing parameters of the drive unit 25.

By using the table of swing parameters vs. permissible temperatures and the table of transmitting conditions vs. maximum saturation temperatures, the system control unit 10 decides the drive voltage that can maximize sensitivity and quality of ultrasound images while keeping the temperature of the probe envelope 29 within a safe limit. Practically, when a swing parameter is designated through the operation unit 11, the system control unit 10 calculates an upper limit of the permissible temperature by using the table of swing parameters vs. permissible temperatures. Next, the system control unit 10 reads out the table of transmitting conditions vs. maximum saturation temperatures corresponded to the transmitting conditions designated through the operation unit 11. The system control unit 10 calculates a maximum drive voltage within the upper limit of the permissible temperature calculated by using the table of transmitting conditions vs. maximum saturation temperatures. When the calculated drive voltage is supplied from the system control unit 10, the transmission/reception unit 16 drives the drive unit 25 at the designated swing parameter so as to drive the ultrasound transducers 21 under the designated transmitting condition by the driving voltage. By these operations, the system control unit 10 can set a drive voltage for driving a mechanical 4D probe 30 or a 2D array probe 40.

Figure 11:
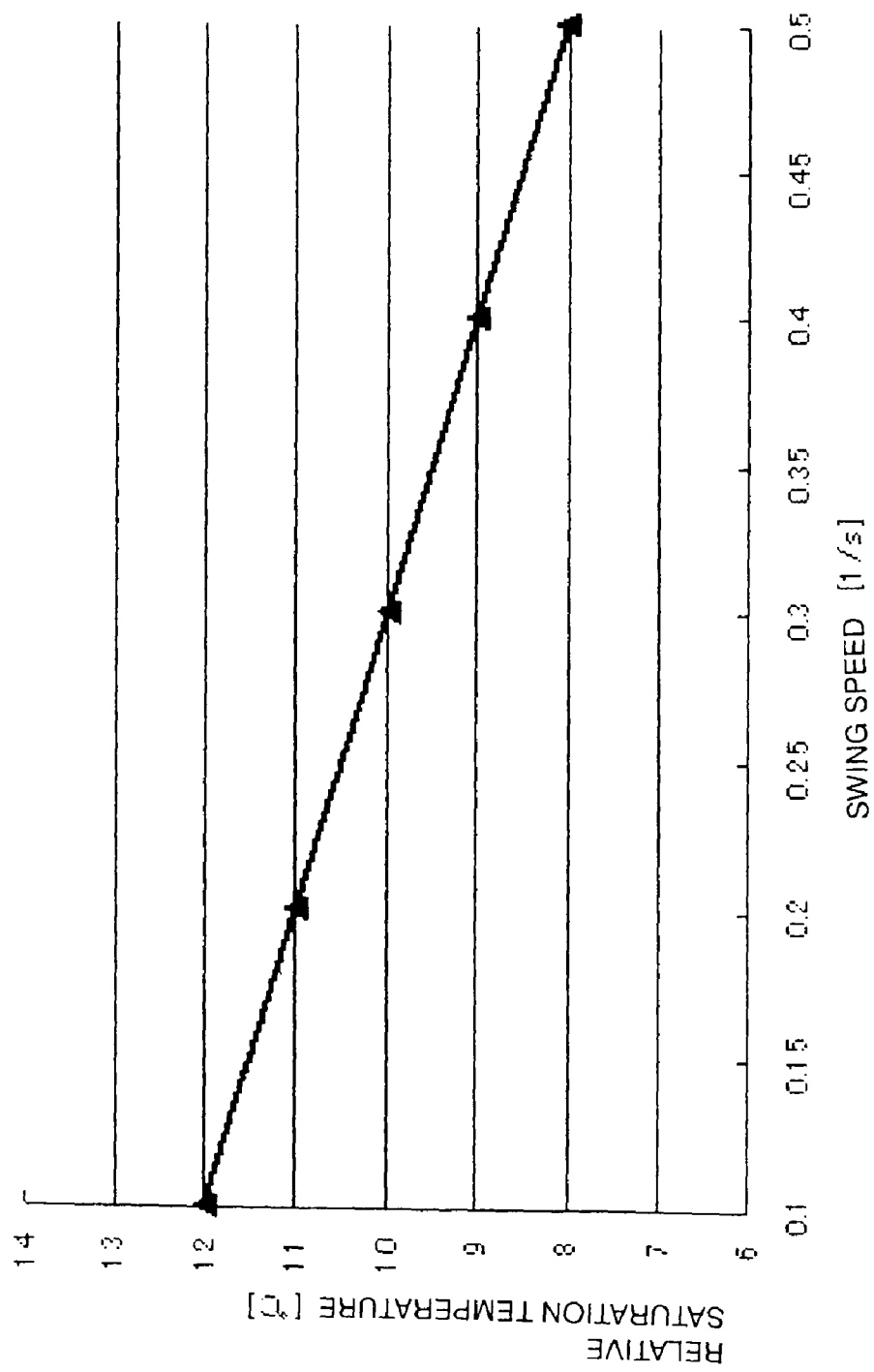
FIG. 11 is a graph depicting relationships between row parameters and relative saturation temperatures.

FIG. 11 shows relationships between the switching speed of the drive board 28 as a row parameter and a relative saturation temperature. The amount of heat generation of the drive board 28 becomes smaller with the swing speed becomes larger. When the heat generation amount of the drive board 28 becomes lower, the relative saturation temperature also goes down and the temperature of the ultrasound transducers 21 goes down.

Figure 12:
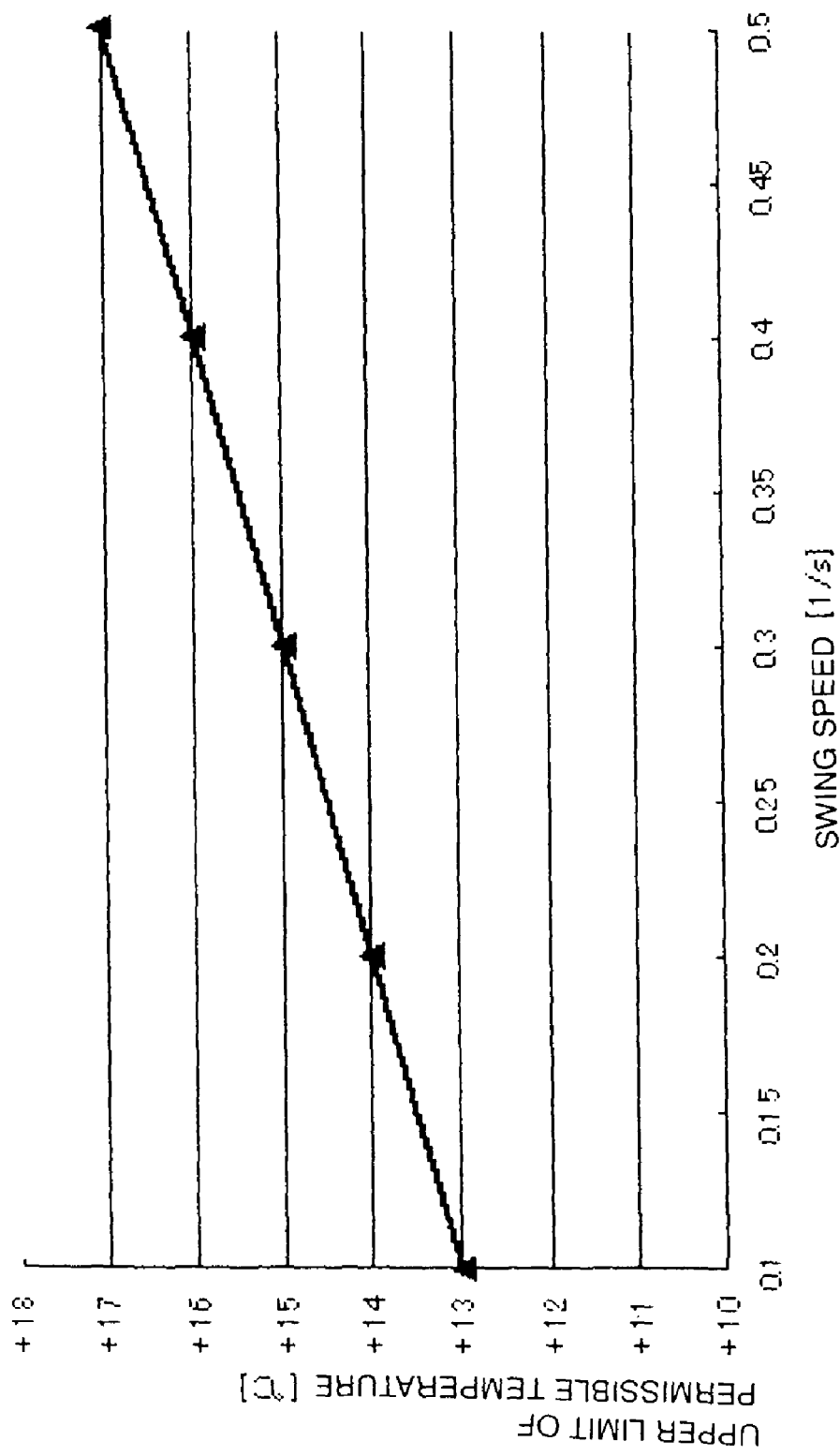
FIG. 12 is a graph depicting relationships between row parameters and upper limits of permissible temperatures.

FIG. 12 shows relationships between the swing speed of the drive board 28 as a row parameter and permissible temperatures. As explained in FIG. 11, the amount of heat generation becomes smaller in proportion to the switching speed of the drive board 28. Consequently, as illustrated in FIG. 12, the permissible temperatures of the ultrasound transducers 21 that can keep an object safe becomes larger in proportion to the switching speed of the drive board 28. The changes of the permissible temperatures are obtained from a difference between a permissible temperature when the probe does not include the drive board 28 and a relative saturation temperature of the drive board 28.

Figure 13:
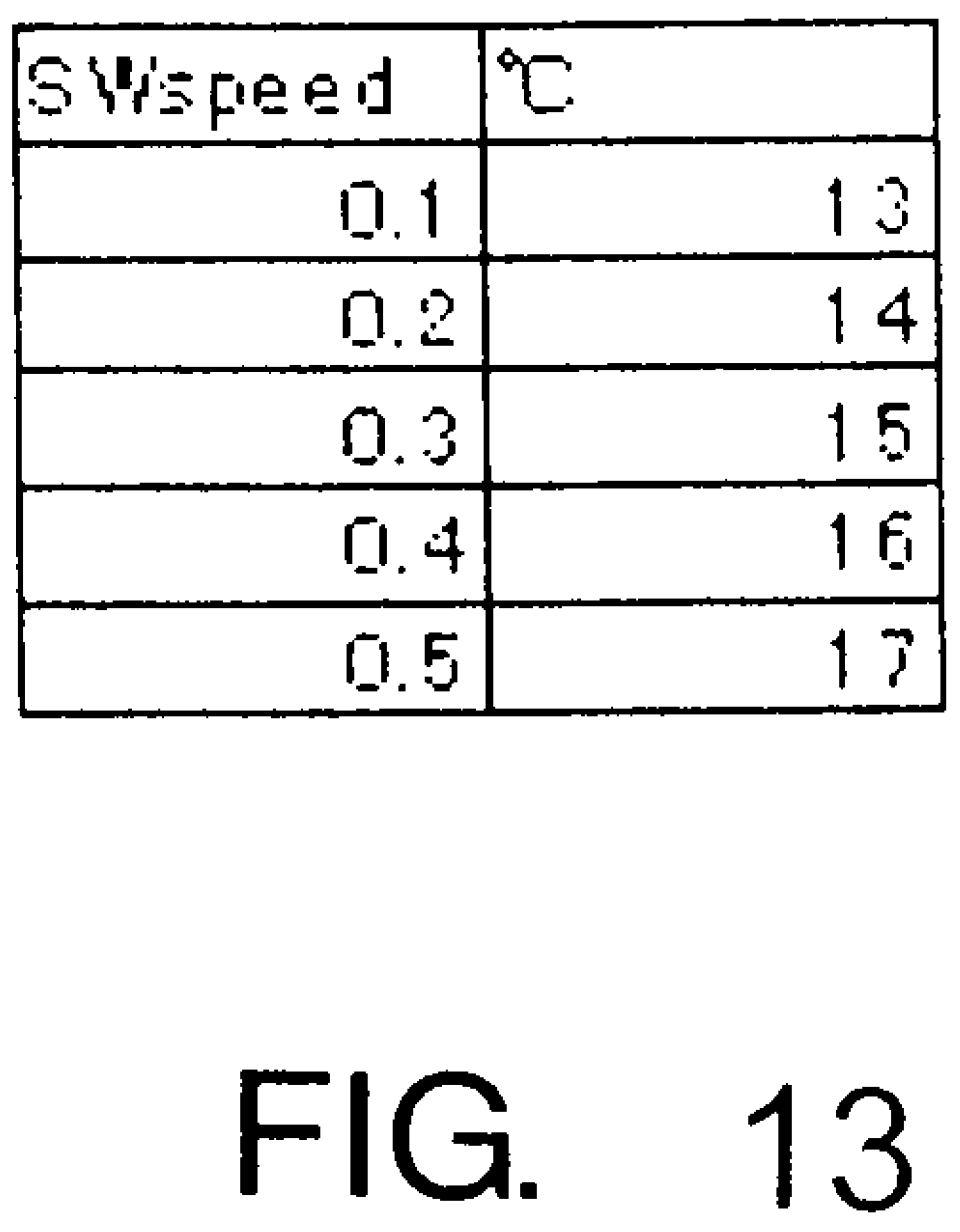

FIG. 13 is an example the table of row parameters vs. permissible temperature. The table of row parameters vs. permissible temperatures records permissible temperatures of the ultrasound transducers 21 in accordance with drive row parameters of a 2D array probe 40. It is also possible to store a plurality of tables of row parameters vs. permissible temperatures in correspondence with other row parameters, such as rows switching order data.

By using these table of row parameters vs. permissible temperatures and table of transmitting conditions vs. maximum saturation temperatures, the system control unit 10 decides a drive voltage for the probe envelope 29 that maximizes sensitivity and quality of image data within a safe range of temperatures. Practically, when a row parameter is designated through the operation unit 11, the system control unit 10 calculates an upper limit value of the permissible temperature by using the table of row parameters vs. permissible temperatures. Then, the system control unit 10 reads out a table of transmitting conditions vs. maximum saturation temperatures corresponding to the transmitting condition designated by the operation unit 11. By using the table of transmitting conditions vs. maximum saturation temperatures, the system control unit 10 calculates a maximum driving voltage within the calculated upper limit of the permissible temperature. Based on the drive voltage calculated by the system control unit 10, the transmission/reception unit 16 drives the drive unit 25 at the designated swing parameter. Further the transmission/reception unit 16 drives the ultrasound transducers 21 under the designated transmitting conditions and the drive voltage.

Figure 14:
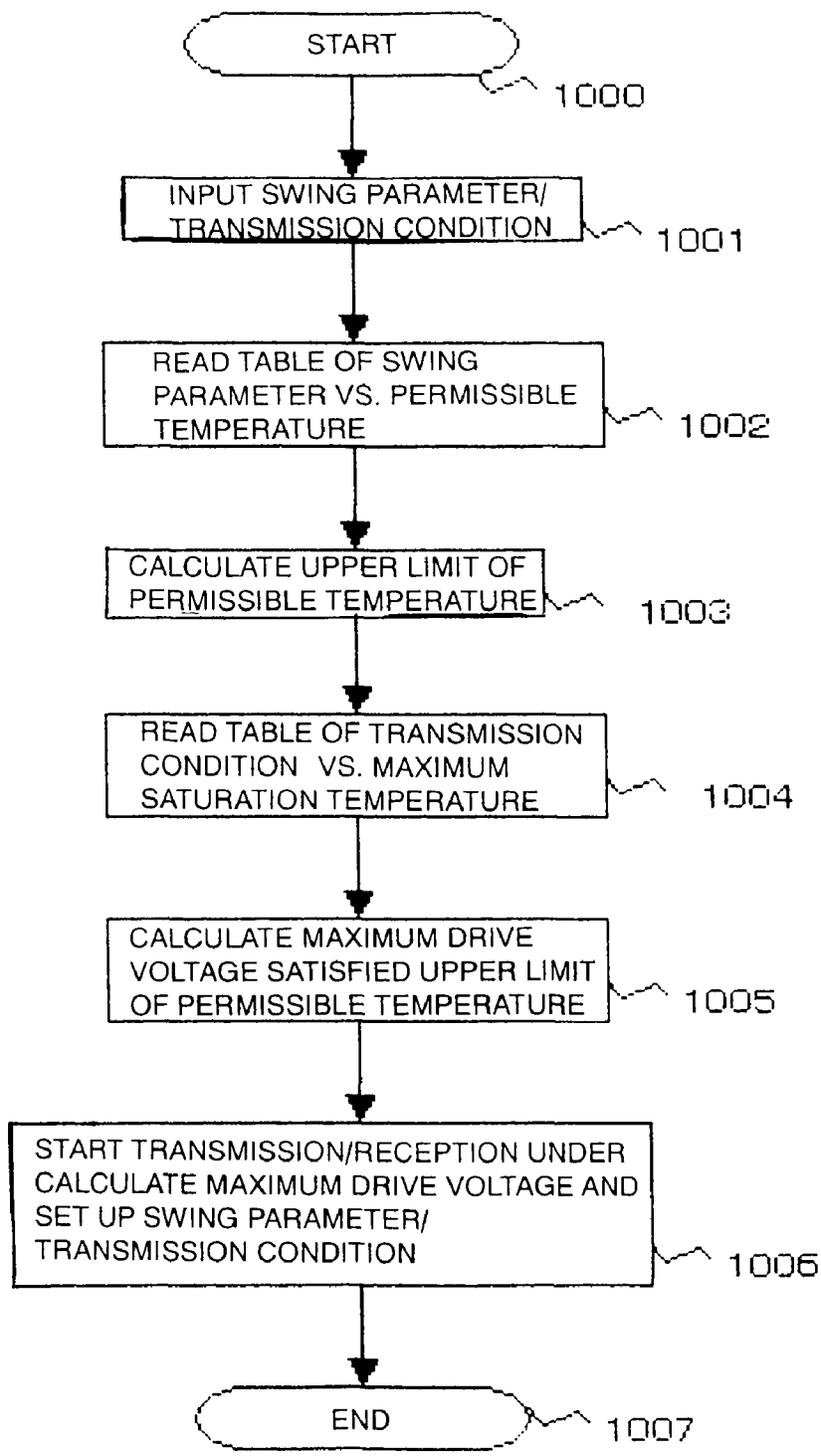
FIG. 14 is a flowchart illustrating a method for setting up transmission conditions consistent with one embodiment.

FIG. 14 is a flowchart illustrating a drive voltage setting method for performing ultrasound transmissions and receptions by using a mechanical 4D probe 30. The drive voltage setting method shown in FIG. 14 is applicable when a 2D array probe 30 is used for the ultrasound transmissions and receptions. In that case, the term "swing parameter" in the method should be replaced "row parameter".

As illustrated in FIG. 14, the system control unit 10 starts the drive voltage setting process (step 1000). Firstly, the system control unit 10 receives swing parameters and transmitting conditions inputted from the operation unit 11 (step 1001). Upon receiving swing parameters and transmitting conditions, the system control unit 10 reads out a table of swing parameters vs. permissible temperatures from the memory unit 12 (step 1002). By reading out the table of swing parameters vs. permissible temperatures, the system control unit 10 calculates a permissible temperature at a designated swing parameter (step 1003). Next, the system control unit 10 reads out a table of transmitting conditions vs. maximum saturation temperatures from the memory unit 12 (step 1004). By reading out the table of transmitting conditions vs. maximum saturation temperatures, the system control unit 10 calculates a maximum driving voltage that fulfils an upper limit value of the permissible temperature calculated under the designated transmitting conditions (step 1005). After calculating the drive voltage, the system control unit 10 drives the probe 20 by using the designated swing parameter and transmitting conditions, and the calculated driving voltage (step 1006), and the process is finished (step 1007).

As explained above, the system control unit 10 performs a calculation process of the maximum drive voltages at the drive parameters and transmitting conditions for the heat sources. The drive parameters of heat sources for a mechanical 4D probe 30 indicate the swing parameters. And the drive parameters of heat sources for a 2D array probe indicate row parameters. By driving the probe at the maximum drive voltage that meets the permissible temperature, it becomes possible to maximize the sensitivity and quality of ultrasound images within a safe temperature range.

The system control unit 10 calculates the drive voltage by combining independent tables for the respective tables of drive parameters vs. permissible temperatures and tables of transmitting conditions vs. maximum saturation temperatures for each of the heat sources. According to the present embodiment, since the independent tables are provided for the respective heat sources, the drive voltage can be easily calculated by combining the independent tables.

In FIG. 14, the drive voltage is calculated by providing the table of drive parameters vs. permissible temperatures of the heat sources in the memory unit 12. The calculation of the drive voltage is not so limited. For instance, instead of using the table of drive parameters vs. permissible temperatures for the heat sources, it is possible to calculate drive voltages by providing a table of drive parameters vs. permissible temperatures for the heat sources. The relative saturation temperature table records temperature changes due to the heat sources when the heat sources are driven by a certain motion parameter.

FIG. 15 is an example of a table of swing parameters vs. relative saturation temperatures for a mechanical 4D probe 30. The table of swing parameters vs. relative saturation temperatures stores associated swing parameters and relative saturation temperatures explained in relation to FIG. 8. The system control unit 10 reads out a relative saturation temperature in accordance with a designated swing parameter through the operation unit 11 and calculates how degrees of temperature will be relatively increased in the ultrasound transducers 21.

The system control unit 10 adds the relative saturation temperature to the table of transmitting conditions vs. maximum saturation temperatures. By adding the relative saturation temperature, it becomes possible to calculate a maximum saturation temperature of the ultrasound transducers 21 in light of heat generation from the drive unit 25. By using the relative saturation temperature added table of transmitting conditions vs. maximum saturation temperatures, the system control unit 10 decides a maximum driving voltage resulting a permissible temperature. As a permissible temperature, a preliminarily decided unique temperature is used.

Figure 16:
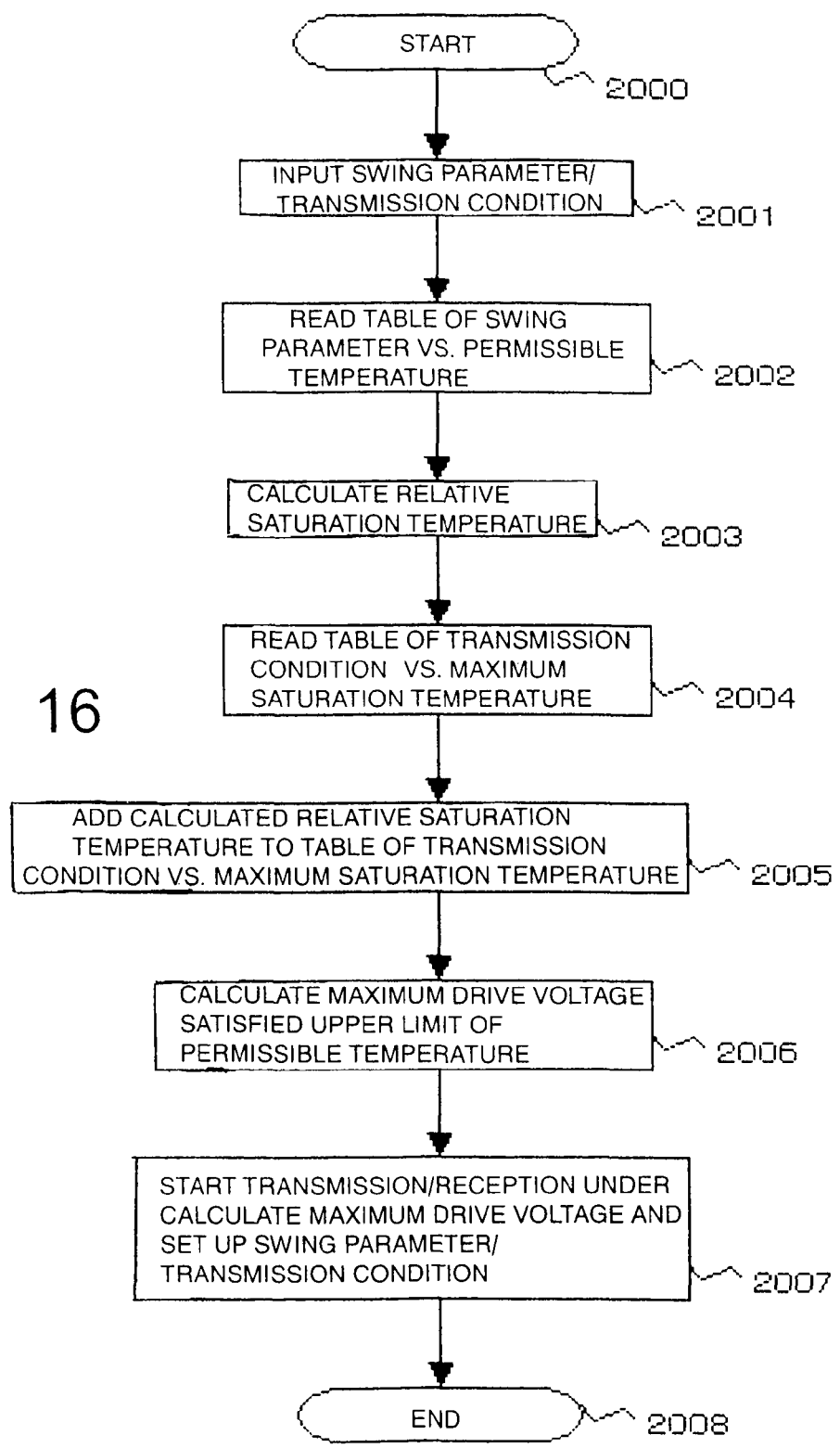
FIG. 16 is a flowchart illustrating a method for setting up transmission conditions consistent with another embodiment.

FIG. 16 is a flowchart illustrating a method for performing ultrasound transmissions and receptions by setting drive voltages for a mechanical 4D probe 30. If a 2D array probe 40, the method for setting the drive voltages shown in FIG. 16 is applicable by changing the term "swing parameter" alone to the term "row parameter".

Firstly, the system control unit 10 starts the process (step 2000). The system control unit 10 receives a swing parameter and a transmitting condition input from the operation unit 11 (step 2001). Upon receiving the swing parameter and the transmitting conditions, the system control unit 10 reads out the table of swing parameters vs. relative saturation temperatures from the memory unit 12 (step 2002). By reading out the table, the system control unit 10 calculates a relative saturation temperature at the designated swing parameter (step 2003). Next, the system control unit 10 reads out a table of transmitting conditions vs. maximum saturation temperature in the memory unit 12 (step 2004). By reading out the table of transmitting conditions vs. maximum saturation temperatures, the system control unit 10 adds the calculated relative saturation temperature to the table value (step 2005). After performing the addition process, the system control unit 10 calculates a maximum driving voltage that meets an upper limit of the permissible temperature by using the added table of transmitting conditions vs. maximum saturation temperature (step 2006). After calculating the drive voltage, the system control unit 10 drives the probe 20 at the designated swing parameter and the transmitting condition by using the calculated drive voltage (step 2007) and finishes the process (step 2008).

In the above-mentioned embodiments, while two heat sources of the ultrasound transducers 21 and the drive unit 25 or the drive board 28 are included in the probe, the number of the heat sources is not limited to this. If a plurality of heat sources causing large temperature changes exist other than as above described, it is possible to respectively store each of the plurality of tables of drive parameters vs. relative saturation temperature in the memory unit 12. The system control unit 10 adds the relative saturation temperature calculated in accordance with each drive parameter to the table of transmitting conditions vs. maximum saturation temperatures. By doing so, even where more than two heat sources other than the ultrasound transducers 21 exist in the probe 20, the drive voltage can be easily calculated.

According to the above explained processes, the system control unit 10 calculates each maximum driving voltage under the drive parameters and transmitting conditions for the designated heat sources. By driving the probe 20 at the maximum driving voltage meeting the permissible temperature, it becomes possible to maximize sensitivity or quality of ultrasound images while guaranteeing a safe temperature for an object.

Further, the system control unit 10 calculates a driving voltage by adding a relative temperature calculated from the table of relative saturation temperature to a value in the table of transmitting conditions vs. maximum saturation temperature. By providing independently each table for the two heat sources, it becomes possible to easily calculate a driving voltage.

The system control unit 10 calculates the maximum saturation temperature by adding relative saturation temperatures calculated from the table of relative saturation temperature. By adding the relative saturation temperatures calculated for each of the heat sources, the maximum saturation temperatures can be easily calculated even when a plurality of heat sources exist in the probe 20.

The above-mentioned embodiments can be modified by combining the plurality of construction elements. For instance, in the above embodiment, the memory unit 12 stores the temperature change data, such as the maximum saturation temperatures, the relative saturation temperatures or the permissible temperatures as the tables. Instead of using the tables, it is also possible to store temperature calculation functions combined with coefficients in the table so as to calculate the maximum saturation temperature, the relative saturation temperature and the permissible temperature at each input time of drive parameters or transmitting conditions of the plurality of heat sources.

In the above described embodiments, the ultrasound transducers 21, the drive unit 25 and the drive board 28 are identified as heat sources in the probe 20. Of course, elements other than these three elements may become the heat sources. For instance, various elements installed in the probe, such as an operation board of the ultrasound transducers 21, cables for transferring electrical signals or a cooling mechanism for circulating air or liquid, can be regarded as heat sources. Thus, the memory unit 12 can store the permissible temperature tables or the relative saturation temperature table for these other elements.

In the present embodiment, the drive voltage only is explained as a motion parameter that is calculated by the system control unit 10. Of course, other various motion parameters, such as, a waveform of drive signals for the ultrasound transducers, currents of the drive signals, powers of the drive signal, input/output intervals of the drive signals, transmitting conditions or drive parameters of the heat sources, can be calculated by using the table.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

The invention claimed is:

1. An ultrasound image diagnosis apparatus comprising;
   an ultrasound probe for transmitting and receiving a plurality of ultrasound waves along prescribed directions to and from an object:
   an input unit configured to input at least one motion parameter for the ultrasound probe, wherein the at least one motion parameter includes at least one ultrasound waveform, a transmission interval, a transmission frequency or a focusing position of the plurality of ultrasound waves;
   said ultrasound probe including a plurality of ultrasound transducers for respectively transmitting and receiving ultrasound waves in accordance with a designated motion parameter including and the drive voltage;
   a drive component installed in the ultrasound probe for swinging the plurality of ultrasound transducers in order to change directions of the ultrasound transmissions and receptions in accordance with swing parameters, wherein the swing parameters includes at least one swing angle, a swing speed and an angular resolution;
   a memory unit configured to store a first temperature change data for associating temperature changes due to the plurality of ultrasound transducers with the motion parameters, and a second temperature change data for associating temperature changes due to the drive component with the swing parameters for the drive component; and a control unit for setting the drive voltage based on the motion parameters, the swing parameters, the first temperature change data and the second temperature change data.

2. An ultrasound diagnosis apparatus including an ultrasound probe for performing transmissions and receptions of ultrasound waves, the ultrasound image diagnosis apparatus comprising:

an ultrasound probe for transmitting and receiving a plurality of ultrasound waves along prescribed directions to and from an object:

an input unit configured to input at least one motion parameter including a driving voltage for the ultrasound probe;

a plurality of ultrasound transducers arranged in two dimensions and installed in the ultrasound probe for performing transmissions and receptions of ultrasound waves in accordance with the at least one motion parameter, wherein the at least one motion parameter includes at least one of an ultrasound transmission wave form, a transmission interval, a transmission frequency or a focusing position of the plurality of ultrasound waves;

a switching unit installed in the probe configured to switch electrical paths for transferring electrical signals to the plurality of ultrasound transducers based on at least one row parameter, wherein the at least one row parameter includes electrical signal transferring path data and a switching speed;

a memory unit configured to store a first temperature change data for associating temperature changes due to the plurality of ultrasound transducers with the at least one motion parameter, and a second temperature change data for associating temperature changes due to the switching unit with at least one row parameter; and a control unit configured to set a drive voltage based on the at least one motion parameter, the at least one row parameter, the first temperature change data and the second temperature change data.

3. The ultrasound diagnosis apparatus according to claim 1, wherein the control unit sets up the drive voltage so as that a sum of a temperature change value based on the first temperature change data and a temperature change value based on the second temperature change data falls within a scope of the permissible temperature.

4. The ultrasound diagnosis apparatus according to claim 2, wherein the control unit sets up the drive voltage so as that a sum of a temperature change value based on the first temperature change data and a temperature change value based on the second temperature change data falls within a scope of the permissible temperature.

5. The ultrasound diagnosis apparatus according to claim 1, wherein the second temperature change data records changes of permissible temperature of the ultrasound transducers due to at least one drive component; and the control unit sets up the drive voltage so as that a temperature rise due to the ultrasound transducers falls within a permissible temperature range.

6. The ultrasound diagnosis apparatus according to claim 1, wherein the drive component comprises a motor configured to change directions of ultrasound transmissions and receptions by swinging the plurality of ultrasound transducers in accordance with the swing parameter.

7. The ultrasound diagnosis apparatus according to claim 1, wherein the ultrasound probe is a mechanical 4D probe.

8. The ultrasound diagnosis apparatus according to claim 2, wherein the ultrasound probe is a 2D array probe.

9. A probe drive voltage setting method for an ultrasound image diagnosis apparatus including an ultrasound probe having a plurality of transducers, a system control unit and a memory unit, the method comprising:

inputting either at least one swing parameter for the plurality of transducers or at least one row parameter for the plurality of transducers;

reading out a table of swing parameters vs. permissible temperatures or a table of row parameters vs. permissible temperatures from the memory unit based on the input;

calculating a limit value of the permissible temperatures from the table of swing parameters vs. permissible temperatures at the designated swing parameter, or a relative saturation temperature of the table of row parameters vs. permissible temperatures at the designated row;

reading out a table of transmission conditions vs. maximum saturation temperatures from the memory;

calculating a maximum drive voltage within the limit value of the permissible temperature or the relative saturation temperature by using a maximum saturation temperature at the input transmission condition; and driving the probe by using the maximum drive voltage and the input swing parameter or the row parameter.

10. The probe drive voltage setting method according to claim 9, wherein the calculation of the maximum drive voltage meeting the upper limit of the permissible temperature is further performed by adding the calculated relative saturation temperature to the values in the table of transmission conditions vs. maximum saturation temperatures.

* * * * *